United States Patent
Miller et al.

(10) Patent No.: US 11,026,966 B2
(45) Date of Patent: Jun. 8, 2021

(54) ANIMAL FEED PRODUCTS CONTAINING PERCARBONATE AND METHODS OF FEEDING SAME

(71) Applicant: PURINA ANIMAL NUTRITION LLC, Shoreview, MN (US)

(72) Inventors: Bill L. Miller, Labadie, MO (US); Thomas Earleywine, Cottage Grove, MN (US); Robert C. Musser, Woodbury, MN (US); Samantha Steelman, Champaign, IL (US)

(73) Assignee: PURINA ANIMAL NUTRITION LLC, Arden Hills, MN (US)

( * ) Notice: Subject to any disclaimer, the term of this patent is extended or adjusted under 35 U.S.C. 154(b) by 0 days.

(21) Appl. No.: 15/969,439

(22) Filed: May 2, 2018

(65) Prior Publication Data
US 2019/0336522 A1 Nov. 7, 2019

(51) Int. Cl.
| | | |
|---|---|---|
| A61K 33/00 | (2006.01) | |
| A23K 20/147 | (2016.01) | |
| A61K 9/00 | (2006.01) | |
| A23K 50/60 | (2016.01) | |
| A23K 20/22 | (2016.01) | |
| A23K 50/10 | (2016.01) | |

(52) U.S. Cl.
CPC ............ *A61K 33/00* (2013.01); *A23K 20/147* (2016.05); *A23K 20/22* (2016.05); *A23K 50/10* (2016.05); *A23K 50/60* (2016.05); *A61K 9/0095* (2013.01)

(58) Field of Classification Search
CPC ...... A23K 20/147; A23K 20/22; A23K 50/10; A23K 50/60; A61K 33/00; A61K 9/0095
See application file for complete search history.

(56) References Cited

U.S. PATENT DOCUMENTS

| | | | |
|---|---|---|---|
| 2,125,398 A | 8/1938 | Reichert et al. | |
| 4,320,116 A | 3/1982 | Bjoerck | |
| 4,617,190 A | 10/1986 | Montgomery | |
| 6,165,532 A | 12/2000 | Mutti et al. | |
| 7,001,741 B1 | 2/2006 | Tanzer et al. | |
| 2003/0207014 A1 | 11/2003 | Larose et al. | |
| 2004/0180126 A1 | 9/2004 | Kies | |
| 2009/0016990 A1 | 1/2009 | Alberte et al. | |
| 2011/0229598 A1 | 9/2011 | Musser | |
| 2011/0281016 A1* | 11/2011 | Beever | A23K 40/00 426/623 |
| 2016/0000104 A1* | 1/2016 | Musser | A23K 20/147 426/2 |

FOREIGN PATENT DOCUMENTS

| | | |
|---|---|---|
| CN | 103271091 A | 9/2013 |
| EP | 2799068 A1 | 11/2014 |
| IL | 47426 A | 4/1978 |
| WO | 2011084794 A1 | 7/2011 |

OTHER PUBLICATIONS

Calf Sessions by Rob Costello, Oct. 3, 2017, "Effect of Acidified Milk Replace on the Calf's Digestive Tract".*
2014 PennState Extension article on Feeding Acidified Milk to Calves.*
"PCT International Search Report dated Aug. 8, 2019, in PCT Application No. PCT/US2019/030179".
"PCT Written Opinion dated Aug. 8, 2019, in PCT Application No. PCT/US2019/030179".
Food & Agriculture Organization, World Health Organization, "Benefits and Potential Risks of the Lactoperoxidase system of Raw Milk Preservation", Report of an FAO/WHO technical meeting; Accessed Feb. 13, 2017, Nov. 28, 2005-Dec. 2, 2005, 73 pages.
Levic, Jovanca et al., "Understanding the Buffering Capacity in Feedstuffs", Biotechnology in Animal Husbandry, 21(5-6), 2005, 309-313.
Lombard, Jason E., "Epidemiology and Economics of Paratuberculosis", Vet. Clin Food Anim 27, 2011, pp. 525-535.
Luckstadt, Christian et al., "Organic acids in animal nutrition", Fefana Publications, 2014.
PCT, "International Search Report and Written Opinion", Application No. PCT/US2015/038612, dated Sep. 23, 2015, 8 pages.

* cited by examiner

*Primary Examiner* — Blessing M Fubura
(74) *Attorney, Agent, or Firm* — Dorsey & Whitney LLP

(57) ABSTRACT

Methods of feeding livestock animals involve feeding the livestock animals a milk replacer comprising percarbonate. The milk replacer has a pH of about 5.8 and the concentration of percarbonate is effective to reduce bacterial growth within the milk replacer product. The milk replacer can also include at least one added organic acid.

13 Claims, 3 Drawing Sheets

300

Feeding the livestock animals a milk replacer comprising percarbonate, wherein the milk replacer has a pH of about 5.8.

*FIG. 3*

ANIMAL FEED PRODUCTS CONTAINING PERCARBONATE AND METHODS OF FEEDING SAME

TECHNICAL FIELD

Implementations relate to feed products and methods of feeding such products to animals. Specific implementations provide percarbonate-containing milk replacers of reduced pH which are effective to impede bacterial growth without reducing palatability.

BACKGROUND

Young animals require adequate nutrition for healthy growth and development. Robust growth early after birth can be especially important for the long-term development of livestock animals. A number of feeding systems have been used to enhance weight gain of livestock beginning at a young age and may include feeding techniques implemented prior to and after weaning. These techniques may involve providing milk replacer products to the animals, but milk replacers are often susceptible to bacterial contamination, which can lead to digestive problems that hinder animal growth. Milk replacers can be especially vulnerable to Salmonella proliferation, and while some milk replacer compositions have been modified to slow Salmonella growth, such products are often ineffective and can be unpalatable to the animals. Improved feed products effective to kill Salmonella without compromising taste are thus desired.

SUMMARY

Implementations provide approaches to feeding young livestock animals that involve providing the animals with a milk replacer composition, which has a reduced pH and is supplemented with percarbonate, that results in the animals exhibiting increased feed intake and improved performance.

In accordance with some examples of the present disclosure, a method of feeding livestock animals may involve feeding the livestock animals a milk replacer comprising percarbonate, wherein the milk replacer has a pH of about 5.8. In some embodiments, the percarbonate comprises sodium percarbonate. In some examples, the livestock animals are calves. In some embodiments, the milk replacer includes at least one added organic acid. In some embodiments, the percarbonate may be present in the milk replacer at a concentration of about 4 lbs. per ton by dry weight of the milk replacer. In some examples, the milk replacer comprises about 18 to about 30 wt % protein and about 15 to about 30 wt % fat by dry weight. In some embodiments, the livestock animals may be fed the milk replacer between birth and about 2 to about 12 weeks of age.

In some examples, in response to ingesting the milk replacer comprising percarbonate, the livestock animals may increase a rate of weight gain relative to animals fed a milk replacer lacking percarbonate and/or having a pH of about 5.2. In some embodiments, in response to ingesting the milk replacer comprising percarbonate, the livestock animals may increase a rate of consumption of the milk replacer relative to animals fed a milk replacer lacking percarbonate and/or having a pH of about 5.2. In some examples, in response to ingesting the milk replacer comprising percarbonate, the livestock animals may increase a rate of consumption of a starter feed relative to animals fed a milk replacer lacking percarbonate and/or having a pH of about 5.2. In some embodiments, the milk replacer may have a reduced concentration of Salmonella over an 8 hour period relative to a milk replacer of pH 5.8 that lacks percarbonate. In some examples, the Salmonella may include one or more strains of Salmonella selected from a group consisting of: S. Heidelberg, S. Dublin, S. Cerro, and S. Montevideo.

In accordance with some examples of the present disclosure, a milk replacer product may include a concentration of percarbonate effective to reduce bacterial growth within the milk replacer product, and at least one organic acid. The organic acid reduces the pH of the milk replacer product to about 5.8.

In some examples, the milk replacer has a reduced concentration of Salmonella over an 8 hour period relative to a milk replacer with a of pH 5.8 that lacks percarbonate. In some embodiments, the at least one organic acid is selected from a group consisting of: citric acid, malic acid, valeric acid, acetic acid, propionic acid, butyric acid, formic acid, caproic acid, oxalic acid, lactic acid, benzoic acid, carbonic acid, phosphoric acid, hydrochloric acid, sulfuric acid, succinic acid, tartaric acid, fumaric acid, adipic acid, gluconic acid, pyrophosphoric acid and/or carbolic acid.

BRIEF DESCRIPTION OF THE DRAWINGS

FIG. 3 is a flow diagram of a method of feeding young animals performed in accordance with principles of the present disclosure.

DETAILED DESCRIPTION

Figure 1:
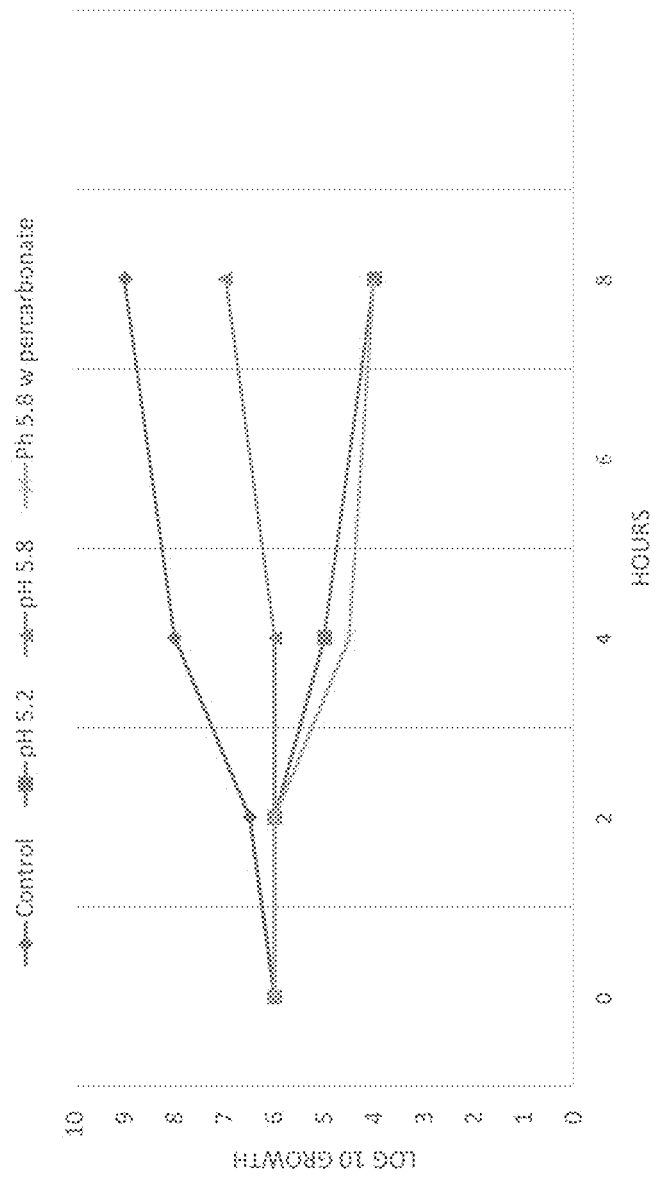
FIG. 1 is a graph of mixed-culture Salmonella growth in various milk replacer products according to principles of the present disclosure.

This disclosure provides methods of feeding young animals a feed product containing percarbonate and having a slightly acidic pH. In embodiments, the feed product can comprise a milk replacer supplemented with sodium percarbonate and having a pH of about 5.8. The percarbonate concentration of the milk replacer may be about 4 lbs. per ton by dry weight in some examples. Methods of feeding the young animals, which may be calves, can involve providing a daily dose of milk replacer containing percarbonate immediately or soon after birth. Providing percarbonate-supplemented milk replacer products to young animals according to the methods described herein may destroy or diminish Salmonella within the milk replacer or at least slow or reduce growth of the bacteria, thereby reducing the incidence of Salmonellosis in the young animals. Milk replacer products described herein may have a higher pH than preexisting milk replacer products formulated to reduce Salmonella growth, and as a result, may be more palatable to young animals, leading to improved animal performance for instance as evidenced by increases in weight gain, milk replacer consumption and/or starter feed intake (Trials 1 and 2). In some examples, the milk replacers disclosed herein may be more effective at controlling Salmonella growth than preexisting, more acidic milk replacers (e.g., pH ~5.2), and may be more palatable to the animals than milk replacers of approximately neutral pH (e.g., pH ~6.8). The antibacterial effect of reducing the milk replacer pH to about 5.2 may be replicated by reducing the pH to about 5.8 and adding percarbonate, indicating that a synergistic effect may be produced via the acidity and percarbonate inclusion in a milk replacer (Trial 3). Feeding methods designed to control Salmonella growth in milk replacers without reducing palatability can involve decreasing the pH of the milk replacer product to about 5.8 and adding percarbonate (Trial 4).

Milk Replacer Products Containing Percarbonate

Milk replacers of the present disclosure can include or be admixed with percarbonate, e.g., sodium percarbonate. Milk replacers may also include or be admixed with one or more acidic components, e.g., organic acids, such that the pH of the liquid milk replacer is less than 7 but more than about 5.2. After evaluating many milk replacers of varying pH and experimenting with various additives, the inventor discovered that a milk replacer containing percarbonate and having a pH ranging from about 5.5 to about 6.0 effectively hinders Salmonella growth and is palatable to young animals fed the milk replacer product. The milk replacer compositions described herein can be palatable despite lacking supplemental palatants that may be added to improve the taste of other feed products. In various examples, milk replacer compositions described herein may not contain lactoperoxidase, e.g., in active form or as an additive.

To reduce the pH of the percarbonate-containing milk replacers disclosed herein, one or more organic acids may be admixed therewith. The specific acids employed may vary, as may the concentrations of the acid[s]. In some embodiments, at least one acid can be in liquid or dry form. Example organic acids that may be utilized alone or in any combination include but are not limited to: citric acid, malic acid, valeric acid, acetic acid, propionic acid, butyric acid, formic acid, caproic acid, oxalic acid, lactic acid, benzoic acid, carbonic acid, phosphoric acid, hydrochloric acid, sulfuric acid, succinic acid, tartaric acid, fumaric acid, adipic acid, gluconic acid, pyrophosphoric acid and/or carbolic acid.

Milk replacers of the present disclosure may be produced according to traditional methods in which the fat and protein components of milk replacers are spray dried and combined into a milk replacer powder comprised of soluble or at least suspendable ingredients. Spray drying processes generally involve maintaining a spray dryer at temperatures between 100° C. to 200° C. so that the spray dried component rapidly heats and loses moisture. Advantageously, percarbonate is a stable powder that remains non-reactive in dry form, making it amenable to admixing with dry milk replacer compositions according to the methods described herein. Pure hydrogen peroxide, by contrast, may not be as stable in powder form.

The milk replacer can be milk and/or vegetable based, and the nutrient profile generally includes fat and protein. The fat content may range from about 2.25 to about 4.7 wt % of the hydrated milk replacer or from about 8 to about 31 wt % of the milk replacer powder. The level of fat may be tailored for a target animal, e.g., calves, as well as the age of the animals fed. In some examples, a calf milk replacer may include a crude fat content ranging from about 10 to about 20 wt % of the powder or about 3 to about 3.75 wt % of the hydrated milk replacer, and full potential calf milk replacers may include fat from about 25 to about 31 wt % of the powder or about 3.75 to about 4.7 wt % of the hydrated milk replacer. In some embodiments, the powdered milk replacer may have a crude fat content of about 8 to about 12 wt %, about 9 to about 11 wt %, about 10 wt %, about 14 to about 20 wt %, about 16 to about 18 wt %, or about 17 wt %.

Predominant fat sources may be lard, tallow, palm kernel, canola oil or coconut oils, alone or in combination, which may contain various amounts of medium chain triglycerides. In addition, some fat from lecithin and residual fat (e.g., butter fat, milkfat, or both) may contribute to the fat content in milk replacers.

Protein in milk replacers typically ranges from about 2.2 to about 5.1 wt % of the hydrated milk replacer or about 18 to about 30 wt % of the powder. For traditional calf milk replacers, the protein content may be about 22 wt % of the powder or about 3.3 wt % of the rehydrated milk replacer, and milk replacers formulated for enhanced performance, such as full potential milk replacers, may include protein at about 25 to about 28 wt % of the powder or about 3.9 wt % to about 4.8 wt % of the rehydrated milk replacer.

Protein may be sourced from animal (e.g., milk, plasma, egg, and red blood cells) and vegetable sources and combinations thereof. Milk-derived protein sources are generally referred to as milk proteins and may include whey, whey protein concentrate, casein, skim milk, sodium caseinate, and calcium caseinate. Non-milk proteins (NMPs), such as vegetable protein (e.g., soy protein, hydrolyzed soy protein, hydrolyzed soy protein modified, soy protein isolate, wheat concentrates, wheat isolates, pea concentrates, pea isolates, and/or potato proteins), animal protein (e.g., plasma such as bovine or porcine plasma, egg and red blood cells), and single cell protein, alone or in combination, may be included as a protein source in the milk replacer. Non-milk proteins may contain varying levels of phosphorous. For instance, phosphorous may be present at about 0.65 wt % of soybean meal, at about 0.78 wt % of soy protein isolate, at about 0.68 wt % of hydrolyzed soy protein modified, at about 1.0 wt % of dehulled canola meal, and each of these components may be present in NMP-containing milk replacers. NMPs may account for up to from 1 to about 65%, from about 50 to about 65%, about 55 to 65%, about 55 to 60%, or up to or at about 60 or about 65% of the total protein content, with the balance of protein derived from milk protein; while milk protein may account for about 35 to 99%, about 35 to about 50%, about 35 to 45%, about 40 to 45%, up to about 40%, or up to about 35% of the total protein content in the milk replacer in some examples.

Methods of Feeding Percarbonate-Containing Milk Replacers of Reduced pH

Methods of feeding animals can involve feeding the animals milk replacer containing various concentrations of percarbonate. Implementations can involve obtaining a percarbonate additive, e.g., sodium percarbonate powder, and admixing it with a milk replacer, in liquid or dry form, just prior to feeding. Alternatively, the milk replacer product may contain the sodium percarbonate in the original composition. Implementations can further involve obtaining at least one acid, e.g. an organic acid, in liquid or dry form, and admixing it with the milk replacer, also in liquid or dry form. In some examples, a combination of glucose oxidase and dextrose can be utilized in addition to or in lieu of percarbonate. According to such examples, the added glucose oxidase cleaves $H_2O_2$ molecules from molecules of dextrose. Milk replacer compositions containing the released $H_2O_2$ molecules, together with at least one added acid, can control Salmonella growth without reducing palatability.

Animals fed according to the methods herein can include dairy calves, chicks, piglets, or foals. The animals can be fed the milk replacer compositions between birth and about 1, 2, 3, 6, 7, 10, 12 or 24 weeks of age, or any sub-period therebetween. The feeding period may begin with the first milk replacer feeding immediately after birth or upon reaching a producer where the animal will be raised (e.g., within a 1-3 days of birth).

The amount of percarbonate admixed with milk replacer can vary depending on the age of the animals fed, the pH of the milk replacer, and/or the actual or anticipated Salmonella concentration within the milk replacer. The amount of percarbonate can be effective in reducing the growth of Salmonella in the liquid milk replacers, or at least impeding or halting growth of the bacteria. In some examples, the amount of percarbonate can be effective to reduce the concentration of Salmonella in a milk replacer inoculated or contaminated with Salmonella. The antibacterial effect of the percarbonate may be supplemented by the reduced pH of the milk replacer, such that the percarbonate and the acidity provide a synergistic antibacterial effect. In various embodiments, the concentration of percarbonate within the milk replacer by dry weight can be about 4 lbs. percarbonate per 1 ton of milk replacer by dry weight. In other examples, the per-ton percarbonate concentration can range from about 0.5 to about 20 lbs., about 1 to about 12 lbs., about 2 to about 6 lbs., about 3 to about 5 lbs., or about 3.5 to about 4.5 lbs. In some examples, the percarbonate concentration may be adjusted one or more times throughout a feeding period. For instance, a higher concentration of percarbonate may be provided to the animals during an initial period after birth, and then decreased one or more times thereafter, for example after about 1, 2, 3, 4, 5, 6, 7, 8, 10 or 12 weeks. Offering the highest concentration of percarbonate early in life may protect the digestive systems of the young animals at a time when they are most susceptible to bacterial infection and the associated negative effects. Rehydration of the percarbonate-supplemented milk replacer composition with water may be beneficial. Sodium percarbonate is very soluble in water, readily dissociating to carbonate ions, sodium ions, and hydrogen peroxide.

The amount and concentration of acid added to the milk replacer to reduce the pH thereof may vary. In some examples, the amount of acid can be effective to provide additional antibacterial properties within the milk replacer without causing a reduction in palatability of the milk replacer. The target pH achieved via acid addition may be below a normal pH of milk ranging from about 6.5-7.0 and above an acidic pH ranging from about 5.0-5.25. In some examples, the final pH of the liquid milk replacer may range from about 5.4 to about 6.2, about 5.6 to about 6.0, about 5.7 to about 5.9, or about 5.8, for example as shown in the method 300 of FIG. 3. Young livestock animals, e.g., calves, may exhibit a substantial preference for milk replacers within this pH range compared to identical milk replacers having a lower pH of about 5.25. In various embodiments, the amount of acid added per ton of milk replacer, by dry weight, may range from about 10 to about 40 lbs., about 10 to about 30 lbs., about 10 to about 20 lbs., about 25 to about 35 lbs., about 28 to about 32 lbs., about 30 lbs., about 10 to about 18 lbs., about 12 to about 16 lbs., or about 14 lbs. In some embodiments, about 14 lbs. of acid may be added to a ton of milk replacer by dry weight to attain a pH of about 5.8. The acid may comprise a combination of two or more acids, such as citric and malic acid.

The animals can be offered a fixed daily ration of milk replacer, which may form all or a portion of the animals' total feed intake. Prior to the onset of weaning, for example for the first 6 weeks after birth, the milk replacer in the feed ration may be offered twice per day, and may generally be divided into equal parts. Milk replacers may be fed in traditional settings at a rate of about 1.25 to about 2.5 lbs., about 1.5 to about 2.2 lbs., about 1.7 to about 1.9 lbs., about 1.8 lbs., about 2.3 to about 2.7 lbs., or about 2.5 lbs. of the milk replacer product per head per day on a dry weight basis.

In some examples, each animal may be fed a daily ration of about 1.8 lbs. of the milk replacer for about the first week after birth, and an increased daily ration, e.g., of about 2.5 lbs., during weeks 2-6 after birth. After week 6, the twice-daily feedings may be reduced to one feeding, for example comprising about 2.5 lbs. of milk replacer by dry weight.

Implementations can further involve providing the young animals with a starter feed on an ad libitum basis. Starter feeds, such as calf starter feeds, may include a mixture of one or more of corn, soybean meal, wheat middlings, oats, molasses, fat, ground cotton seed hulls, distillers grains, calcium carbonate, salt, and macronutrients and micronutrients. The starter feed may contain about 45 to about 50 wt % coarse ingredients such as corn, soy and oats; about 16 to 22 wt % protein; about 2 to 3 wt % fat, about 5 to 6 wt % fiber (determined on a NIR basis); about 7 wt % acid detergent fiber; and/or about 6 wt % molasses, the balance including a mixture of other nutrients.

After an initial period of feeding the young animals a percarbonate-containing milk replacer of reduced pH, e.g., between birth and about 1, 2, 3, 4, 5, 6, 7, 8, 10, or 12 weeks, the animals can be switched to a diet free of percarbonate-containing milk replacer of reduced pH. Such a diet may comprise regular feedings of a liquid milk replacer and/or a starter feed. Additional feed materials, e.g., grains and/or forages, can also be provided on a regular or ad libitum basis. In some examples, the young animals may be weaned immediately or shortly after the final feeding of percarbonate-containing milk replacer of reduced pH. In some examples, calves can be fed a percarbonate-supplemented milk replacer twice a day for the first 6 to 7 weeks after birth, after which the calves may be switched to a diet free of such a milk replacer. In some examples, calves can be fed a percarbonate-supplemented milk replacer twice a day for the first 2 to 3 weeks after birth, when Salmonella may pose the greatest threat to animal health. Providing a percarbonate-containing milk replacer of reduced pH during an initial feeding period after birth, e.g., about 2 to 3 weeks or up to about 6 to 7 weeks, may improve the calves' early performance in a manner that also enhances long-term growth, thereby increasing the value of the resulting adult cattle for beef or dairy operations. After this initial period, the animals may be fed a conventional milk replacer lacking added percarbonate and/or acid. In some examples, the animals may be weaned after this initial period, such that decreased amounts of conventional milk replacer, or no milk replacer at all, are provided to the animals.

Feeding young animals the disclosed milk replacer products supplemented with percarbonate and having a reduced pH according to the methods herein may improve animal performance. In various embodiments, providing calves with a percarbonate-containing milk replacer of reduced pH (e.g., pH ~5.8) between birth and about 7 weeks of age, or up to about 12 weeks of age, less than 7 weeks of age, or any period therebetween, may increase total weight gain, milk replacer intake, and intake of a concurrently-fed starter feed composition compared to calves fed a similar milk replacer of approximately neutral pH and lacking percarbonate. In some examples, calves offered a percarbonate-containing, reduced pH milk replacer also exhibited an average increase in total starter feed consumption of nearly 22% relative to animals provided with the neutral pH control. Increases in weight gain, milk replacer intake, and intake of a concurrently-fed starter feed composition observed in calves offered a percarbonate-containing milk replacer of pH 5.8 may also be observed relative to calves offered a milk replacer of pH 5.2 and no percarbonate, which while exhibiting comparable antibacterial effects, causes reduced palatability. For example, calves fed a neutral milk replacer (which may actually cause less weight gain, milk replacer intake and starter feed intake than the percarbonate-containing milk replacer of pH 5.8) may consume more of the milk replacer, e.g., by about 5%, and a starter feed, e.g., by about 24%, compared to calves fed an acidic milk replacer of pH 5.2-5.25.

Salmonella concentrations may also be reduced in such milk replacers relative to milk replacers of reduced pH, e.g., 5.8, that do not contain percarbonate. This bacterial reduction may decrease the incidence of Salmonellosis in young animals, especially young livestock animals such as calves. For example, adding percarbonate to a milk replacer and reducing its pH to about 5.8 may cause about a 2 $\log_{10}$ decrease in CFU/ml of a mixed culture of Salmonella over an 8-hour incubation period. The same percarbonate-supplemented, reduced pH milk replacer may cause about a 6 $\log_{10}$ decrease in growth of a single strain of S. Heidelberg over an 8-hour incubation period, e.g., at about 38° C. The reduction in bacterial infection and digestive conditions may also reduce the mortality rate of young livestock animals.

Implementations of the present disclosure are more particularly described in the following calf trials for illustrative purposes only. Numerous modifications and variations are within the scope of the present disclosure as will be apparent to those skilled in the art.

Examples

Trial 1

This study was conducted to assess the palatability of liquid milk replacer products having different acidity levels.

The test subjects evaluated in this 10-day trial included eight calves ranging in age from 3-7 days. Each calf was simultaneously offered three quarts (0.75 lbs. milk replacer powder) of a non-acidified liquid milk replacer having an approximately neutral pH of 6.8 and three quarts of an acidified liquid milk replacer having pH of 5.25. Both milk replacers were based on the Land O'Lakes Warm Front PB formulation, which includes 27 wt % protein and 10 wt % fat. The different milk replacer products were offered in separate pails, the location of which were switched for each feeding to eliminate bias, and the milk product replenished daily. When approximately half of the total milk product was consumed for each calf, the pails were removed and the non-consumed product weighed. Data collected during the first two days of the trial were excluded from the statistical analysis. The calves were also offered a calf starter feed containing 20 wt % crude protein on an ad libitum basis. Table 1, below, shows the average preference data for the calves on a per-feeding basis.

TABLE 1

|  | lbs/hd/feeding | preference ratio | P-value | preference incidence |
|---|---|---|---|---|
| Neutral pH | 4.733 | 3.43:1.00 | <0.00001 | 79.5 |
| Acidic pH | 1.382 | | | 18.9 |

Table 1 shows that the calves significantly preferred the neutral milk replacer over the acidic milk replacer at each feeding by a ratio of 3.43:1. As captured by the preference incidence, the calves preferred the neutral milk replacer in 79.5% of feedings, and the acidic milk replacer in only 18.9% of the feedings (the milk replacers were equally consumed in 1.6% of feedings). Accordingly, lowering the pH of a milk replacer to 5.25 reduces palatability to young calves.

Trial 2

This study was conducted to assess the palatability of liquid milk replacer products of different acidity levels and the impact of such products on animal performance.

The test subjects evaluated in this six-week trial included 48 Holstein bull calves sourced from Wisconsin and ranging in age from 3-7 days. Initial weights and gamma globulin levels of the calves were measured prior to beginning the experiment. Each calf was simultaneously offered a non-acidified liquid milk replacer of approximately neutral pH (pH ~6.8) and an acidified liquid milk replacer (pH ~5.25). Both milk replacers were based on the Land O'Lakes Amplifier Max formulation, which includes 22 wt % protein and 20 wt % fat. The calves were fed the milk replacers through two identical auto-feeding systems (Förster Technik, Engen, Germany) that were programmed to provide two pounds of milk replacer solids per calf. The calves were also offered a calf starter feed containing 20 wt % protein on an ad libitum basis. The results from the feeding trial are shown below in Table 2.

TABLE 2

| Performance Parameters | Neutral | Acidic | p value (if <.2) | SE |
|---|---|---|---|---|
| initial Ig | 4.47 | 4.33 | — | 0.24 |
| initial weight | 92.1 | 91.0 | — | 1.40 |
| weight at day 42 | 140.9 | 135.3 | — | 3.59 |
| Gain (lbs.) | | | | |
| avg. gain wks. 1&2 | 10.58 | 9.24 | — | 1.36 |
| avg. gain wk. 3 | 10.74 | 12.24 | — | 0.87 |
| avg. gain wk. 4 | 9.95b | 6.62a | 0.02 | 0.98 |
| avg. gain wk. 5 | 10.32 | 10.14 | — | 0.82 |
| avg. gain wk. 6 | 7.26 | 6.05 | — | 1.25 |
| avg. total gain | 48.84 | 44.29 | — | 3.01 |
| CMR consumption (lbs.-dry) | | | | |
| avg. CMR consumption wks. 1&2 | 21.35b | 19.06a | 0.04 | 0.77 |
| CMR consumption wk. 3 | 13.48 | 13.22 | — | 0.21 |
| CMR consumption wk. 4 | 13.54 | 13.33 | — | 0.22 |
| CMR consumption wk. 5 | 13.42 | 13.14 | — | 0.22 |
| CMR consumption wk. 6 | 6.99 | 6.61 | 0.10 | 0.16 |
| avg. total CMR consumption | 68.78 | 65.36 | 0.06 | 1.23 |
| Starter Consumption (lbs.-dry) | | | | |
| avg. starter consumption wks. 1&2 | 1.05 | 0.59 | — | |
| avg. starter consumption wk. 3 | 1.96 | 1.29 | — | |
| avg. starter consumption wk. 4 | 3.13 | 2.29 | — | |
| avg. starter consumption wk. 5 | 4.45 | 4.83 | — | |
| avg. starter consumption wk. 6 | 14.67 | 11.44 | — | |
| avg. total starter consumption | 25.25 | 20.43 | — | |
| overall feed:gain ratio | 2.08 | 2.06 | — | 0.12 |

Table 2 shows that, on average, the calves fed the neutral milk replacer consumed more of the milk replacer (about 5% more) and the starter feed (about 24% more) compared to the calves fed the acidic milk replacer. Notably, early milk replacer consumption (weeks 1 and 2) was significantly less (p<0.04) for the calves fed the acidic milk replacer, indicating that the calves' preference for non-acidic formulations may be particularly strong early after birth. As a result, growth of the calves fed the acidic milk replacer was delayed (total gain reduced by 9.3%). The results thus confirm that when offered milk replacers differing only in pH (5.25 vs. 6.8), calves prefer the more basic option (pH ~6.8), evidenced by greater consumption of the preferred product and greater weight gain. The calves also consumed more of a concurrently-fed starter feed, potentially as a result of the higher caloric needs caused by faster growth.

Trial 3

This study was conducted to assess the impact of pH and percarbonate inclusion on Salmonella growth in milk replacers.

In this trial, milk replacer products differing in pH and/or percarbonate inclusion were evaluated in identical conditions. A milk replacer comprised of 26 wt % protein (all milk protein) and 20 wt % fat and having a pH in the range of 6.8-7.0 served as the control medium. The test products included a milk replacer of pH 5.2, a milk replacer of pH 5.8, and a milk replacer of pH 5.8 that also included percarbonate. Two Salmonella incoculates known to cause calf mortality, sourced from the University of Wisconsin Veterinary Diagnostic Lab, were used to separately contaminate the milk replacer samples. The first inoculum comprised a mixed culture of S. Dublin, S. Cerro and S. Montevideo, and the second inoculum consisted of a single strain of S. Heidelberg. Each dry milk replacer was reconstituted with sterile deionized water and placed in a 15 ml round-bottom tube. Each of the S. Dublin, S. Cerro, and S. Montevideo strains was grown overnight in trypticase soy broth on a rotating rack at 35° C. until the culture reached a density of about $10^9$ CFU/ml. The bacterial cells were harvested by centrifugation, washed, and then diluted in PBS and added either as a cocktail of strains (the first inoculum) or a single strain (the second inoculum) to each milk replacer sample at approximately $10^6$ CFU/ml. Each milk replacer sample was incubated at 38.5° C. and the samples were removed after 2, 4 and 8 hours to determine the Salmonella concentration in CFU/ml. The results are shown below in Tables 3A and 3B, as well as FIGS. 1 and 2.

TABLE 3A

| | | Time | | | | |
|---|---|---|---|---|---|---|
| | | 0 hours | 2 hours | 4 hours | 6 hours | 8 hours |
| Mixed *Salmonella* Culture ($Log_{10}$ Growth) | Control | 6 | 6.5 | 8 | 8.5 | 9 |
| | pH 5.2 | 6 | 6 | 5 | 4.5 | 4 |
| | pH 5.8 | 6 | 6 | 6 | 6.5 | 7 |
| | pH 5.8 + percarbonate | 6 | 6 | 4.5 | 4.25 | 4 |

The data shown in Table 3A shows that when inoculated into the control milk replacer, the mixed culture of Salmonella strains increased 3 $log_{10}$ CFU over the eight-hour incubation period, reaching a final concentration of about $10^9$ CFU/ml. Salmonella grew to a lesser extent in the pH 5.8 milk replacer, reaching a final concentration of about $10^7$ CFU/ml, thus indicating that milk replacer having a reduced pH of about 5.8 may be effective to slow the growth of Salmonella relative to a milk replacer of approximately neutral pH. The percarbonate-containing milk replacer of pH 5.8 resulted in an approximately 2 $log_{10}$ decrease in CFU/ml during the incubation period. Accordingly, the percarbonate-supplemented milk replacer having a pH of about 5.8 was more effective in controlling the growth of a mixed culture of Salmonella than a milk replacer of pH 5.8 that is not supplemented with percarbonate. The percarbonate-supplemented milk replacer of pH 5.8 reduced log 10 growth by approximately the same amount as the non-percarbonate milk replacer of pH 5.2.

The numerical data provided in Table 3A is shown in graphical form in FIG. 1. The graph clearly illustrates the increase in Salmonella growth observed in the control sample, the approximately stagnant Salmonella concentration of the pH 5.8 milk replacer, and the similar reduction in Salmonella growth observed in milk replacers having a pH of 5.2 and percarbonate-containing milk replacers having a pH of 5.8.

TABLE 3B

| | | Time | | | | |
|---|---|---|---|---|---|---|
| | | 0 hours | 2 hours | 4 hours | 6 hours | 8 hours |
| *Salmonella* Heidelberg Culture ($Log_{10}$ Growth) | Control | 8 | 8.5 | 8 | 8.5 | 9 |
| | pH 5.2 | 8 | 7 | 5 | 3.5 | 2 |
| | pH 5.8 | 8 | 8 | 6 | 6.25 | 6.5 |
| | pH 5.8 + percarbonate | 8 | 5 | 2 | 2 | 2 |

The data shown in Table 3B shows that a percarbonate-supplemented milk replacer having a pH of about 5.8 is also more effective in controlling the growth of a single-strain culture of S. Heidelberg than a milk replacer of pH 5.8 that is not supplemented with percarbonate. Specifically, the percarbonate-supplemented milk replacer of pH 5.8 caused a 6 $log_{10}$ decrease in growth of S. Heidelberg, which was approximately the same decrease observed in the pH 5.2 milk replacer sample inoculated with the same bacterial strain. Bacterial growth in the milk replacer having a pH of 5.8, but not supplemented with percarbonate, also decreased, but to a lesser extent, i.e., about 1.5 $log_{10}$.

Figure 2:
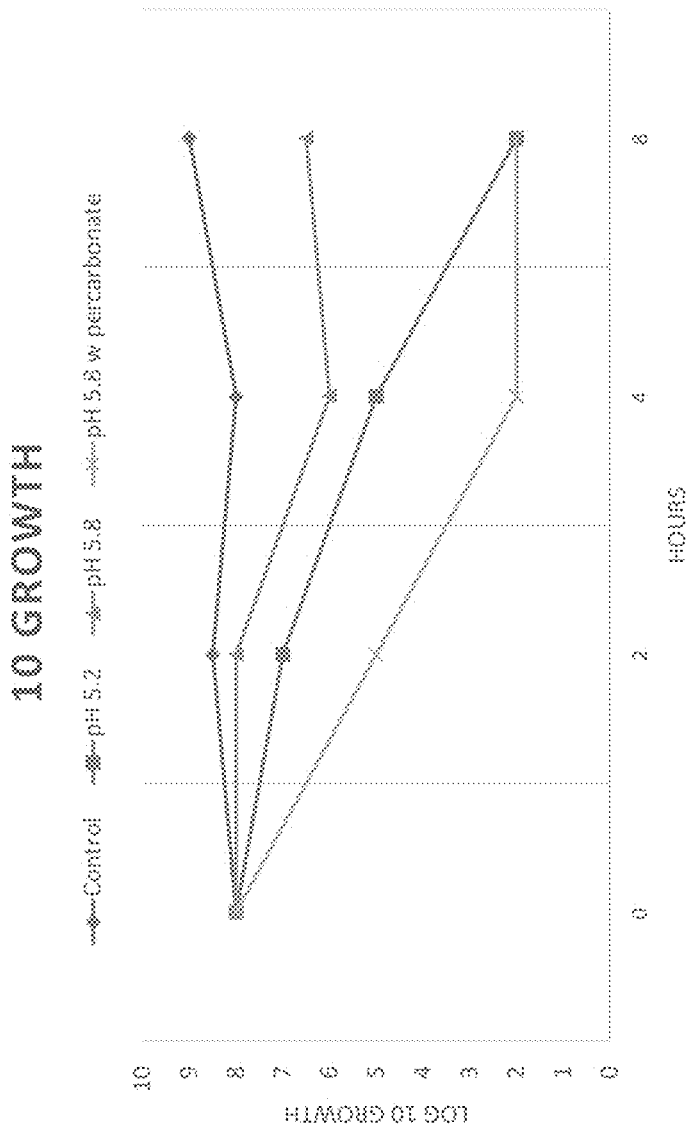
FIG. 2 is a graph of Salmonella Heidelberg growth in various milk replacer products according to principles of the present disclosure.

The numerical data provided in Table 3B is shown in graphical form in FIG. 2. The graph illustrates the increase in Salmonella concentration observed in the control sample, the decrease in Salmonella concentration of the pH 5.8 milk replacer, and the similar, more drastic reduction in Salmonella growth observed in milk replacers having a pH of 5.2 and percarbonate-containing milk replacers having a pH of 5.8.

Together, the data shown in Tables 3A and 3B, along with FIGS. 1 and 2, show that Salmonella growth in a milk replacer can be impeded, and the bacterial concentration reduced, by decreasing the pH of the milk replacer to about 5.2 or reducing the pH to about 5.8 and supplementing it with percarbonate. Accordingly, the antibacterial effect of reducing the pH to about 5.2 may be replicated by reducing the pH to about 5.8 and adding percarbonate, indicating a synergistic effect of the acidity and percarbonate in a milk replacer.

Trial 4

This study was conducted to assess the palatability of liquid milk replacer products of different acidity levels and percarbonate content and the impact of such products on animal performance.

The test subjects evaluated in this seven-week trial included 32 Holstein bull calves sourced from Wisconsin and ranging in age from 3-7 days. Initial weights and gamma globulin levels of the calves were measured prior to beginning the experiment. Each calf was assigned to one of two treatments. The control treatment was a non-acidified liquid milk replacer (pH ~6.8) and the test treatment was a similar milk replacer containing sodium percarbonate and having a pH of about 5.8. The inclusion rate of sodium percarbonate was about 4 lbs. per ton of milk replacer powder. Organic acids were used to reduce the pH of the test treatment to 5.8.

Both milk replacer formulations were based on the Land O'Lakes Cold Front formulation, which includes 27 wt % protein and about 20 wt % fat. Each calf was fed a daily ration of 1.8 lbs. of milk replacer during days 1-7 of the experiment, and a daily ration of about 2.5 lbs. during days 7-42. The milk replacer was provided twice daily through day 42, and then once a day through day 49. The calves were also offered a calf starter feed containing 22 wt % protein on an ad libitum basis throughout the trial.

TABLE 4

| Performance Parameters | pH 6.8 | pH 5.8 + percarb. | p value (if <.2) | SE |
|---|---|---|---|---|
| initial Ig | 3.77 | 3.60 | — | 0.33 |
| initial weight | 100.7 | 99.3 | — | 2.58 |
| weight at week 7 | 185.2 | 189.1 | — | 4.34 |
| Gain (lbs.) | | | | |
| avg. gain wks. 1&2 | 14.62 | 17.89 | 0.11 | 1.41 |
| avg. gain wk. 3 | 12.65 | 12.19 | — | 0.98 |
| avg. gain wk. 4 | 12.88 | 12.97 | — | 0.89 |
| avg. gain wk. 5 | 13.20 | 14.95 | 0.10 | 0.73 |
| avg. gain wk. 6 | 15.22 | 15.96 | — | 1.16 |
| avg. gain wk. 7 | 15.92 | 15.91 | — | 1.93 |
| avg. total gain | 84.5 | 89.9 | — | 3.26 |
| CMR consumption (lbs.-dry) | | | | |
| CMR consumption wks. 1&2 | 27.15 | 28.39 | 0.16 | 0.60 |
| CMR consumption wk. 3 | 16.95 | 17.11 | — | 0.26 |
| CMR consumption wk. 4 | 17.42 | 17.48 | 0.16 | 0.03 |
| CMR consumption wk. 5 | 17.09a | 17.50b | 0.01 | 0.08 |
| CMR consumption wk. 6 | 17.43 | 17.50 | — | 0.04 |
| CMR consumption wk. 7 | 8.72 | 8.75 | 0.14 | 0.01 |
| total CMR consumption | 104.8 | 106.7 | 0.10 | 0.82 |
| Starter Consumption (lbs.-dry) | | | | |
| starter consumption wks. 1&2 | 0.71 | 0.47 | — | 0.23 |
| starter consumption wk. 3 | 0.77 | 1.29 | — | 0.33 |
| starter consumption wk. 4 | 1.53 | 1.81 | — | 0.44 |
| starter consumption wk. 5 | 2.64 | 3.40 | — | 0.68 |
| starter consumption wk. 6 | 5.63 | 7.44 | — | 1.11 |
| starter consumption wk. 7 | 16.25 | 19.06 | — | 1.99 |
| total starter consumption | 27.52 | 33.47 | — | 4.44 |
| Average feed:gain | 1.57 | 1.57 | — | 0.03 |

As shown in Table 4, average total weight gain was greater in calves fed the percarbonate-containing milk replacer of pH 5.8, as was the average total milk replacer consumption and starter feed consumption. Milk replacer consumption of the percarbonate-containing, reduced pH milk replacer was significantly greater in week 5 of the trial, and the average weight gain exhibited by the calves during weeks 1 and 2 was also substantially greater for calves fed the percarbonate-containing, reduced pH milk replacer. Calves fed the percarbonate-containing, reduced pH milk replacer also exhibited an average increase in total starter feed consumption of nearly 22% relative to animals provided with the neutral pH control. The feed:gain ratio was the same for animals fed the control milk replacer and the percarbonate-containing milk replacer of pH 5.8. Trial 4 thus indicates that total weight gain, milk replacer intake and starter feed intake are not reduced, and are actually increased, when a milk replacer of pH 5.8 is fed to calves relative to a milk replacer of pH 6.8, provided the acidic milk replacer also contains sodium percarbonate. Accordingly, an improved method of controlling Salmonella growth in milk replacer without reducing palatability involves decreasing the pH of the product to about 5.8 and adding percarbonate.

As used herein, the term "about" modifying, for example, the quantity of a component in a composition, concentration, and ranges thereof, employed in describing the embodiments of the disclosure, refers to variation in the numerical quantity that can occur, for example, through typical measuring and handling procedures used for making compounds, compositions, concentrates, or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities.

Similarly, it should be appreciated that in the foregoing description of example embodiments, various features are sometimes grouped together in a single embodiment for the purpose of streamlining the disclosure and aiding in the understanding of one or more of the various aspects. These methods of disclosure, however, are not to be interpreted as reflecting an intention that the claims require more features than are expressly recited in each claim. Rather, as the following claims reflect, inventive aspects lie in less than all features of a single foregoing disclosed embodiment, and each embodiment described herein may contain more than one inventive feature.

Although the present disclosure provides references to preferred embodiments, persons skilled in the art will recognize that changes may be made in form and detail without departing from the spirit and scope of the invention.

What is claimed is:

1. A method of feeding livestock animals, the method comprising:
    feeding the livestock animals a milk replacer comprising an antibacterial system consisting of percarbonate and at least one added acid selected from a group consisting of: citric acid, malic acid, valeric acid, acetic acid, propionic acid, butyric acid, formic acid, caproic acid, oxalic acid, lactic acid, benzoic acid, carbonic acid, phosphoric acid, hydrochloric acid, sulfuric acid, succinic acid, tartaric acid, fumaric acid, adipic acid, gluconic acid, pyrophosphoric acid and carbolic acid, wherein the milk replacer has a reduced pH of about 5.8,
    wherein the milk replacer exhibits reduced growth of Salmonella over a period of about 2 to about 8 hours relative to a milk replacer of pH 5.8 that lacks percarbonate.

2. The method of claim 1, wherein the percarbonate comprises sodium percarbonate.

3. The method of claim 1, wherein the livestock animals are calves.

4. The method of claim 1, wherein the percarbonate is present in the milk replacer at a concentration of about 4 lbs. per ton by dry weight of the milk replacer.

5. The method of claim 1, wherein the milk replacer comprises about 18 to about 30 wt % protein and about 15 to about 30 wt % fat by dry weight.

6. The method of claim 1, wherein the livestock animals are fed the milk replacer between birth and about 2 to about 12 weeks of age.

7. The method of claim 1, wherein in response to ingesting the milk replacer comprising percarbonate, the livestock animals increase a rate of weight gain relative to animals fed a milk replacer lacking percarbonate and/or having a pH of about 5.2.

8. The method of claim 1, wherein in response to ingesting the milk replacer comprising percarbonate, the livestock animals increase a rate of consumption of the milk replacer relative to animals fed a milk replacer lacking percarbonate and/or having a pH of about 5.2.

9. The method of claim 1, wherein in response to ingesting the milk replacer comprising percarbonate, the livestock animals increase a rate of consumption of a starter feed relative to animals fed a milk replacer lacking percarbonate and/or having a pH of about 5.2.

10. The method of claim 1, wherein the Salmonella comprises one or more strains of Salmonella selected from a group consisting of: S. Heidelberg, S. Dublin, S. Cerro, and S. Montevideo.

11. The method of claim 1, wherein the milk replacer comprises about 8 to about 31 wt % fat by dry weight.

12. A milk replacer product comprising:
an antibacterial system consisting of percarbonate and at least one acid selected from a group consisting of: citric acid, malic acid, valeric acid, acetic acid, propionic acid, butyric acid, formic acid, caproic acid, oxalic acid, lactic acid, benzoic acid, carbonic acid, phosphoric acid, hydrochloric acid, sulfuric acid, succinic acid, tartaric acid, fumaric acid, adipic acid, gluconic acid, pyrophosphoric acid and carbolic acid, wherein a concentration of percarbonate is effective to reduce bacterial growth within the milk replacer product;
wherein the at least one acid reduces the pH of the milk replacer product to about 5.8,
wherein the milk replacer product exhibits reduced growth of Salmonella over a period of about 2 to about 8 hours relative to a milk replacer product of pH 5.8 that lacks percarbonate.

13. The milk replacer product of claim 12, wherein the concentration of percarbonate is about 4 lbs. per ton by dry weight of the milk replacer.

\* \* \* \* \*